United States Patent

Wentland

Patent Number: 5,334,595
Date of Patent: Aug. 2, 1994

[54] PYRAZOLOQUINOLONES AS ANTICANCER AGENTS

[75] Inventor: Mark P. Wentland, Colonie, N.Y.

[73] Assignee: Sterling Winthrop Inc., New York, N.Y.

[21] Appl. No.: 967,470

[22] Filed: Oct. 23, 1992

[51] Int. Cl.$^5$ .................. C07D 471/04; A61K 31/44
[52] U.S. Cl. ......................... 514/293; 546/82
[58] Field of Search ..................... 546/82; 514/293

[56] References Cited

U.S. PATENT DOCUMENTS

| | | | |
|---|---|---|---|
| 4,312,870 | 1/1982 | Yokoyama | 514/293 |
| 4,524,146 | 6/1985 | Yokoyama | 546/82 |
| 4,602,014 | 7/1986 | Yokoyama | 514/215 |
| 4,959,363 | 9/1990 | Wentland | 514/235.2 |
| 5,075,319 | 12/1991 | Lesher et al. | 514/312 |

FOREIGN PATENT DOCUMENTS

WO91/0628  5/1991  PCT Int'l Appl. .......... 546/82

Primary Examiner—Alan L. Rotman
Attorney, Agent, or Firm—Richard A. Hake; Paul E. Dupont

[57] ABSTRACT

Compounds of the formula

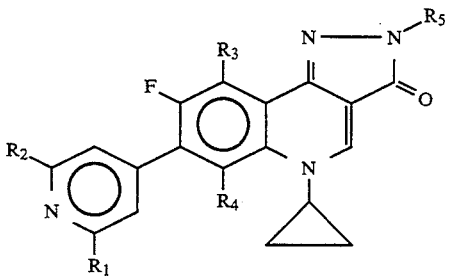

wherein
$R_1$ is hydrogen, lower-alkyl, or trifluoromethyl;
$R_2$ is lower-alkyl, trifluoromethyl or $CH_2Y$ where Y is hydroxy, chloro, lower-alkylamino or dilower-alkylamino
$R_3$ and $R_4$ are each independently hydrogen or fluoro;
$R_5$ is hydrogen, lower-alkyl or
  (a) phenyl, 2-pyridyl, 4-pyridyl, 1-naphthyl or such groups substituted with one or more, the same or different, lower-alkyl, fluoro, hydroxy, or lower-alkoxy;
  (b) cycloalkyl or cycloalkyl substituted with amino, lower-alkylamino, dilower-alkylamino, formamido, acetamido, lower-alkyl, hydroxy, lower-alkoxy, trifluoromethyl, carboxy, lower-alkoxycarbonyl or halo, or cycloalkyl having a phenyl ring fused thereto;
  (c) A saturated heterocyclic 5- or 6-membered ring containing oxygen and/or nitrogen or such ring substituted with lower-alkyl; or
  (d) $(CH_2)_n$-Z wherein n is an integer from about one to four and Z is amino, dilower-alkylamino, bis(hydroxylower-alkyl)lower-alkylamino; or a pharmaceutically acceptable acid addition salt thereof are topoiosmerase II inhibitors and are useful in the treatment of cancer in mammalian hosts.

16 Claims, No Drawings

PYRAZOLOQUINOLONES AS ANTICANCER AGENTS

BACKGROUND OF THE INVENTION a) Field of the Invention

This invention relates to novel pyrazolo [4,3-c]quinolin-3-ones, and to pharmaceutical compositions of these compounds and a method of use thereof as anticancer agents.

b) Information Disclosure Statement

Yokoyama, U.S. Pat. No. 4,312,870, issued Jan. 26, 1982, discloses (2-aryl-pyrazolo[4-3-]quinolin-3-ones of formula:

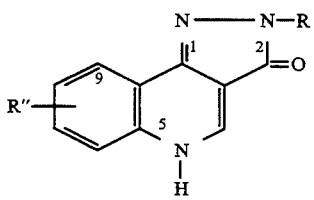

wherein

R is phenyl, R"-phenyl, pyridyl, alkylpyridyl or halopyridyl;

R" is hydrogen, alkyl, alkoxy, alkylthio, OH, halo, $CF_3$, nitro, amino, mono-or dialkylamino, CN, carbamoyl or carboxy; and pharmaceutically acceptable acyl derivatives or salts thereof, which are stated to be psychoactive agents Yokoyama, U.S. Pat. No. 4,524,146, issued Jun. 18, 1985, discloses pyrazolo[4,3-c]quinolon-3-ones of the formula

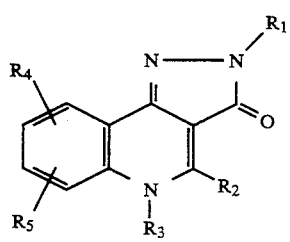

wherein $R_1$ is an aromatic heterocyclic radical selected from quinolyl, isoquinolyl, pyrimidyl and thiazolyl, or such said heterocyclic radical mono- or di-substituted lower alkyl-, lower alkoxy or halogen;

$R_2$ and $R_3$ each independently represents hydrogen or lower alkyl, and $R_4$ and $R_5$ each independently represent hydrogen, lower alkyl, lower-alkoxy, halogen or trifluoromethyl; and pharmaceutically acceptable salts thereof, which are stated to be benzodiazepine receptor modulators.

Yokoyama, U.S. Pat. No. 4,602,014, issued Jul. 22, 1985, discloses compound of the formula

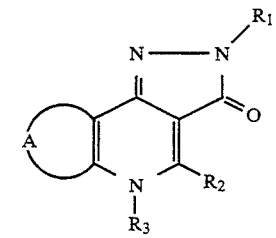

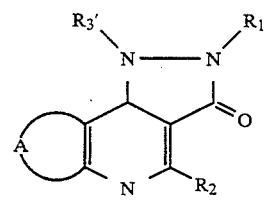

wherein

A is an optionally substituted saturated divalent grouping which together with the two carbon atoms to which is is attached represents a fused 5-, 6-, or 7-membered carbocyclic or heterocyclic ring selected from optionally substituted fused cyclopenteno, cyclohexeno, cyclohepteno, dihydrothieno, dihydropyrano, tetrahydrooxepino, dihydropyrrolo, tetrahydropyrido and tetrahydroazepino;

$R_1$ is lower alkyl, phenyl, or phenyl mono- or disubstituted by lower alkyl, lower alkoxy, halogen or trifluoromethyl; or $R_1$ is an aromatic heterocyclic radical selected from e.g. optionally substituted pyridyl, quinolyl, isoquinolyl, pyrimidyl and thiazolyl;

$R_2$, $R_3$ and $R_3$, are hydrogen or lower alkyl; and pharmaceutically acceptable salts are useful as benzodiazepine receptor modulators for the treatment of nervous system disorders. Pharmaceutical compositions, methods of preparation and certain intermediates stated to be useful as benzodiazepine receptor modulators are also disclosed.

International Patent Application Publication No. WO91/06298, published May 16, 1991, discloses the use of 2,5-dihydro-2-phenyl-3H-pyrazolo(4,3c) quinolin -3-one or its pharmaceutically acceptable alkali metal or acid salts for treating inflammatory and allergic diseases.

Wentland, U.S. Pat. No. 4,959,363, issued Sep. 25, 1990, discloses compounds of the formula

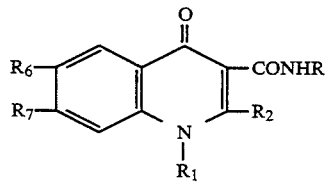

wherein

R is hydrogen, hydroxy, amino or lower-alkyl;

$R_1$ is lower-alkyl, lower-alkenyl, cycloalkyl, pyridinyl, phenyl or substituted phenyl $R_2$ is hydrogen, amino or hydroxy;

$R_6$ is hydrogen or fluoro; and $R_7$ is phenyl, pyridinyl or selected other heterocycles; which are stated to have antiviral activity against herpes virus.

Lesher et al., U.S. Pat. No. 5,075,319, dated Dec. 24, 1991, from an application filed Sep. 13, 1989, discloses fluorinated 1-cyclopropyl-7-(substituted-pyridinyl)-1,4-dihydro-4-oxo-3-quinolinecarboxylic acids of the formula

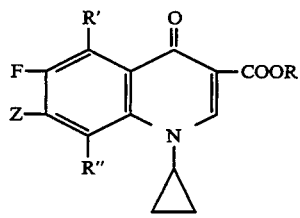

wherein

R is hydrogen;

R' and R" are hydrogen or fluoro, or other groups; and

Z is 3- or 4-pyridinyl substituted by alkyl groups or substituted alkyl groups. The compounds are stated to be superior antibacterial agents.

SUMMARY OF THE INVENTION

In one aspect, the invention relates to novel 2-$R_5$-5-cyclopropyl-8-fluoro-6-$R_4$-9-$R_3$-2,5-dihydro-7-(2-$R_2$-6-$R_1$-4-pyridinyl)-3H-pyrazolo-[4,3-c]-quinolin-3-ones useful as antineoplastic agents.

In a second aspect, the invention also relates to a pharmaceutical composition containing as an active ingredient an antineoplastic effective amount of a compound of the invention.

In a third aspect, the invention relates to a method of inhibiting the growth of or killing malignant cells which comprises administering to a mammal afflicted with malignant cells a compound of the invention in an antineoplastic effective amount to inhibit the growth of or induce the regression of these cells.

DETAILED DESCRIPTION INCLUSIVE OF PREFERRED EMBODIMENTS

As used herein, the term lower-alkyl refers to a straight or branched alkyl radical of 1 to about 6 carbon atoms including, for example, methyl, propyl, isopropyl, sec-butyl, pentyl, n-butyl, 3-hexyl and the like. The term lower-alkoxy refers to a straight or branched alkoxy radical with from 1 to about 4 carbon atoms such as methoxy, ethoxy, propoxy, isopropoxy, butoxy, sec-butoxy and the like.

Cycloalkyl refers to a cyclic hydrocarbon radical of about 4 to about 7 carbon atoms, for example, cyclobutyl, cyclopentyl, cyclohexyl, cycloheptyl and the like. Cycloalkyl having a phenyl ring fused thereto is exemplified by 1,2,3,4-tetrahydronaphthyl, 2,3-dihydroindenyl and the like.

As used herein the term halo or halogen refers to the common halogens, for example, fluoro, chloro, bromo or iodo.

Saturated heterocyclic 5- or 6-membered rings containing oxygen and/or nitrogen include, for example, pyrrolidinyl, morpholinyl, piperidinyl, and the like. These saturated heterocyclic radicals may be N- or C-substituted with lower-alkyl. When bonded directly to the pyrazoloquinolone, the point of attachment of the 5- or 6-membered saturated heterocycle is a ring carbon atom thereof. When bonded to the pyrazoloquinolone through an alkylene group (as Z in the group ($CH_2)_nZ$), the point of attachment of the heterocycle can be either a ring carbon or nitrogen atom thereof.

Specifically, the present invention relates to compounds of formula I

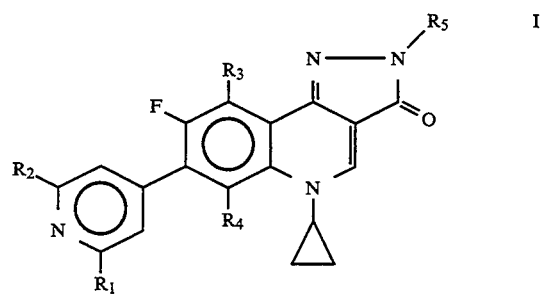

wherein $R_1$ is hydrogen, lower-alkyl, or trifluoromethyl;

$R_2$ is lower-alkyl, trifluoromethyl or $CH_2Y$ where Y is hydroxy, chloro, lower-alkylamino or dilower-alkylamino $R_3$ and $R_4$ are each independently hydrogen or fluoro;

$R_5$ is hydrogen, lower-alkyl or (a) phenyl, 2-pyridyl, 4-pyridyl, 1-naphthyl or such groups substituted with one or more, the same or different, lower-alkyl, fluoro, hydroxy, or lower-alkoxy;

(b) cycloalkyl or cycloalkyl substituted with amino, lower-alkylamino, dilower-alkylamino, formamido, acetamido, lower-alkyl, hydroxy, lower-alkoxy, trifluoromethyl, carboxy, lower-alkoxycarbonyl or halo, or cycloalkyl having a phenyl ring fused thereto;

(c) A saturated heterocyclic 5- or 6-membered ring containing oxygen and/or nitrogen or such ring substituted with lower-alkyl; or (d) $(CH_2)_n$-Z wherein n is an integer from about one to four and Z is amino, dilower-alkylamino, bis(hydroxylower-alkyl)lower-alkylamino, hydroxy, trifluoromethyl, carboxy, lower-alkoxycarbonyl, lower-alkoxy, formyl or acetal thereof, or a substituent selected from (a), (b) or (c) ; or a pharmaceutically acceptable acid addition salt thereof.

Preferred compounds of formula 1 are those wherein $R_1$ and $R_2$ are methyl, $R_3$ is hydrogen, $R_4$ is fluoro and $R_5$ is as defined above.

Compounds of formula I may be prepared according to the following scheme;

Scheme 1

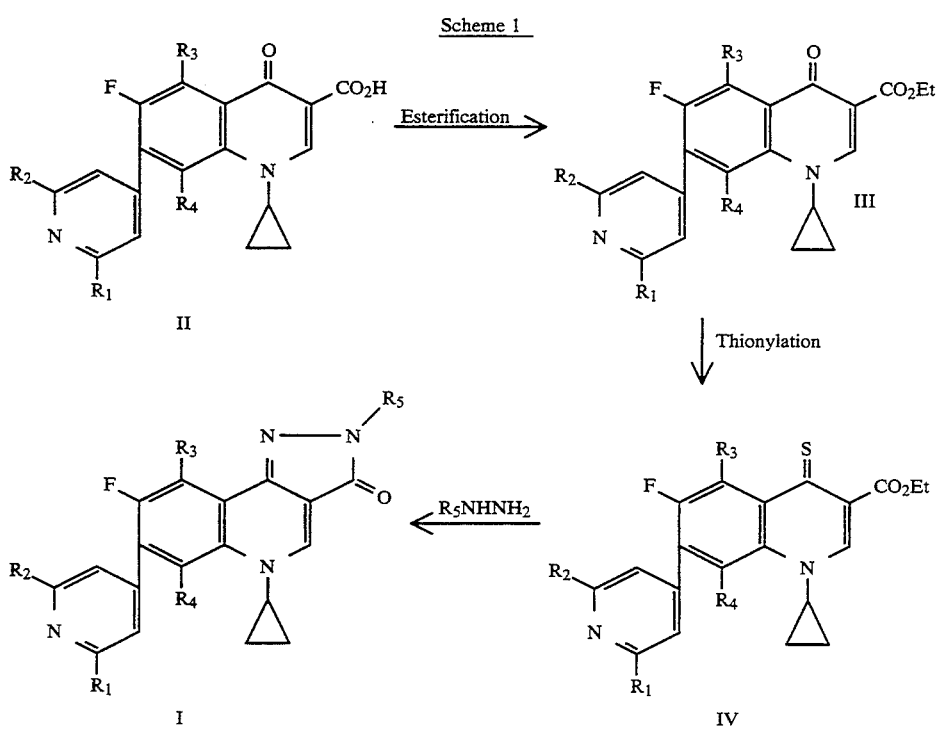

As the scheme illustrates, quinoline carboxylic acid II, described in U.S. Pat. No. 5,075,319, which is incorporated herein by reference, is protected by esterification using methods well known in the art; for example, the acid and lower-alkanol, such as methanol or ethanol, can be refluxed with 1', 1 carbonyldiimidazole, or in the presence of a catalytic amount of a strong acid, e.g. sulfuric acid.

In a preferred method, this protected quinolone III is then thionylated using, for example, [2,4-bis-(4-methoxyphenyl)-1,3-dithia-2,4-diphosphotane-2,4-disulfide] (Lawesson's reagent), $P_4S_{10}$ and the like, in an inert solvent between ambient temperature and the boiling point of the solvent, yielding an intermediate of formula IV.

This intermediate is then reacted with an appropriate hydrazine, or substituted hydrazine ($R_5NHNH_2$) in an inert solvent, for example acetonitrile or DMF, at a temperature between ambient and the boiling point of the solvent, preferably in the presence of a catalytic amount of base, for example pyridine and the like, yielding a compound of formula I.

The hydrazines, $R_5NHNH_2$, are generally known and are commercially available or are prepared by methods well known in the art.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; cleavage of methyl or benzyl ethers to produce the corresponding alcohols or phenols; and hydrolysis of esters or amides to produce the corresponding acids, alcohols or amines as desired can be carried out.

The compounds of the invention are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anion. In practicing the present invention, it is convenient to form the hydrochloride, fumarate, toluenesulfonate, hydrogen sulfate, methanesulfonate or maleate salts and the like. However, other appropriate medicinally acceptable salts within the scope of the invention are those derived from other mineral acids and organic acids. The acid-addition salts of the basic compounds are prepared either by dissolveing the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC).

The following examples illustrate the invention, but do not limit it thereto.

In the following example preparations, diethyl ether is referred to as ether. All reactions were run in dried solvents and under a nitrogen atmosphere.

PREPARATION OF INTERMEDIATES

Preparation 1

Ethyl 1-cyclopropyl-6,8-difluoro-1,4-dihydro-7-(2,6-dimethyl-4-pyridinyl)-4-oxo-3-quinolinecarboxylic acid Formula III $R_1=R_2=CH_3$, $R_3$=hydrogen, $R_4$=fluoro (Intermediate 1)

1,1'-Carbonyldiimidiazole (CDI) (3.9 g, 0.024 mol) was added to a suspension of (6.0 g, 0.016 mol) 1-cyclopropyl-7-(2, 6-dimethyl-4-pyridinyl)-6, 8-difluoro-1,4-dihydro-4-oxo-3-quinolinecarboxylic acid, described in U.S. Pat. No. 5,075,319, and incorporated herein by reference, in DMF (40 mL) and the mixture was stirred at 100° C. for 2 hr under a $N_2$ atmosphere. The resulting solution was cooled to 25° C., diluted with and 60 mL ethanol and heated at reflux 17 h. Removal of the solvents in vacuo gave a residue that was stirred in 20 mL ethanol; after cooling in ice a solid separated and was collected (5.5 g, 86%); a 4.5 g portion of this material was recrystallized from ethanol to give 4.25 of ethyl 1-cyclopropyl-7-(2,6-dimethyl-4-pyridinyl)-6,8-difluoro-1,4-dihydro-4-oxo-3-quinolinecarboxylate, mp 193°–195° C.

Preparation 2

Ethyl 1-cyclopropyl-6,8-difluoro-1,4-dihydro-7-(2,6-dimethyl-4-pyridinyl)-4-thioxo-3-quinolinecarboxylate (Formula IV $R_1=R_2=CH_3$, $R_3$=hydrogen, $R_4$=fluoro) (Intermediate 2)

Lawesson's reagent (25.2 g, 0.06 mol) was added to a solution of ethyl 1-cyclopropyl-7-(2,6-dimethyl-4-pyridinyl)-6, 8-difluoro-1,4-dihydro-4-oxo-3-quinolinecarboxyate (24.1 g, 0.06 mol) in 720 mL THF and the mixture heated at reflux for 21 h. The solvent was removed in vacuo and the residue purified by column chromatography (silica gel 97:3/CHCl$_3$:2-propylamine) to give 26.1 g of product. Recrystallization from ethyl acetate gave ethyl 1-cyclopropyl-7-(2,6-dimethyl-4-pyridinyl)-6, 8-difluoro-1,4-dihydro-4-thioxo-3-quinolinecarboxylate (21.0 g, 84%); mp 194°–195° C.

EXAMPLE 1 (METHOD A)

5-Cyclopropyl-6,8-difluoro-2,5-dihydro-2-[2-(dimethylamino)-ethyl]-7-(2,6-dimethyl-4-pyridinyl)-3H-pyrazolo[4,3-c]quinolin-3-one (E)-2-butendioate (1:1). 2-(Dimethylamino)ethyl hydrazine (7.7 g, 0.0186 mol) was added to a solution of Intermediate 2 (5.0 g,) 0.045 mol) in 46 mL DMF and the resulting solution was heated at 100° C. for 3 h. The mixture was cooled in ice and a solid was collected and washed with ether to give 5.3 g (65%) of product which was treated with fumaric acid (2.72 g, 0.0234 mol) in ethanol to give 6.7 g (54%) of the (E)-2-butendioate salt of a compound of formula I [$R_1=R_2=CH_3$, $R_3$=hydrogen, $R_4$=fluoro, $R_5=(CH_2)_2N(CH_3)_2$], mp 224°–226° C.

EXAMPLE 2 (METHOD B)

4-Cyclopropyl-6,8-difluoro-2, 5-dihydro-2-(2,2,2-trifluoroethyl)-7-(2,6-dimethyl-4-pyridinyl)-3H-pyrazolo[4,3-c]quinolin-3-one. A solution of Intermediate 2 (0.31 g, 0.75 mmol), 2,2,2-trifluoroethyl hydrazine (0.33 g, 2.19 mmol) and 3 mL pyridine was heated at 100° C. for 2 h. An additional 0.30 g of 2,2,2-trifluoroethyl hydrazine was added and heating was continued for 10 h. The resulting mixture was concentrated and purified using silica gel chromatography to provide 0.27 g (79%) of a compound of formula I [$R_1=R_2=CH_3$, $R_3$=hydrogen, $R_4$=fluoro, $R_5=CH_2CF_3$], mp 255°–257° C.

EXAMPLE 3 (METHOD C)

5-Cyclopropyl-6,8-difluoro-7-(2,6-dimethyl-4-pyridinyl)-2, 5-dihydro-2-(2-propyl)-3H-pyrazolo[4,3-c]quinolin-3-one. A mixture of Intermediate 2 (0.50 g, 0.0012 mol), isopropyl hydrazine.$2CH_3CO_2H$ (1.88 g, 0.006 mol) and 4-dimethylaminopyridine (0.88 g, 0.0072 mol) was heated at 120° C. for 2 h and cooled. The resulting mixture was partitioned between CHCl$_3$ and water; the organic layer was washed with brine, dried over Na$_2$SO$_4$ and concentrated in vacuo. The crude product was purified using silica gel chromatography to give 0.11 g (23%) of a compound of formula I [$R_1=R_2=CH_3$, $R_3$=hydrogen, $R_4$=fluoro, $R_5=CH(CH_3)_2$], mp 202°–204° C.

EXAMPLE 4 (METHOD D)

2-(1-Butyl)-5-cyclopropyl-6,8-difluoro-2,5-dihydro-7-(2,6-dimethyl-4-pyridinyl)-3H-pyrazolo[4,3-c]quinolin-3-one. A mixture of Intermediate 2 (0.70 g, 0.0017 mol) n-butyl hydrazinc oxalate (0.80 g, 0.0045 mol), triethylamine (1.0 mL) and 4 mL DMF was heated at 100° C. for 7 h. The mixture was cooled and concentrated and the crude product was purified using silica gel chromatography to give 0.30 g (43%) of a compound of formula I [$R_1=R_2=CH_3$, $R_3$=hydrogen, $R_4$=fluoro, $R_5=(CH_2)_3CH_3$]; mp 164°–165° C.

EXAMPLE 5 (METHOD E)

5-Cyclopropyl-6,8-difluoro-2,5-dihydro-2-(2-hydroxyphenyl)-7-(2,6-dimethyl-4-pyridinyl)-3H-pyrazolo[4,3-c]quinolin-3-one. A solution of Example 32 (0.24 g, 0.51 mmol) in 6 mL CH$_2$Cl$_2$ at −78° C. was treated with BBr$_3$ (0.20 mL). After stirring at −78° C. for 15 min and 25° C. for 90 min, the mixture was treated with 5 mL of 10% NaOH and diluted with water. To this mixture methylene chloride was added followed by 4 mL acetic acid. The CH$_2$Cl$_2$ layer was dried over Na$_2$SO$_4$ and concentrated. The crude product was purified by silica gel chromatography to give 0.19 g (83%) of a compound of formula I [$R_1=R_2=CH_3$, $R_3$=hydrogen, $R_4$=fluoro, $R_5$=2-HO-C$_6$H$_4$], mp 232°–233° C.

EXAMPLES 6–55

The following compounds of formula I wherein $R_1=R_2=CH_3$, $R_3$=hydrogen, $R_4$=fluoro, were prepared from Intermediate 2 by reaction with an appropriate hydrazine, $R_5NHNH_2$, substantially as described in examples 1–4, (methods A–D respectively), and methoxy-containing compounds of formula I were converted to the corresponding hydroxy compounds as described in Example 5 (Method E). In the table, recrystallizing solvents are abbreviated as follows: ethyl acetate (EA), methylene chloride (CH$_2$Cl$_2$), hexanes (hex), isopropanol (i-PrOH), ethanol (EtOH) and diethyl ether (Et$_2$O). In cases where no recrystallizing solvent is indicated recrystallization was not carried out. Melting points are of the free base unless otherwise specified. The notation (d) refers to decomposition at the temperature listed, and (S) indicates that the melting point listed is that of the methanesulfonate salt prepared by the procedure used in method A, substituting methane sulfonic acid for fumaric acid. The hydrazines used are commercially available, known or prepared by known methods.

TABLE I

Compounds of Formula I ($R_1=R_2=CH_3$, $R_3=H$, $R_4=F$)

| Example | $R_5$ | mp (°C.) | method | yld (%) | recrystalizing solvent |
|---|---|---|---|---|---|
| 6 | H | >310 | A | 97 | |
| 7 | $CH_3$ | 242–243 | A | 35 | |
| 8 | $C(CH_3)_3$ | 219–221 | D | 48 | EA |
| 9 | $CH_2CO_2Et$ | 204–206 | D | 64 | |
| 10 | $CH_2CH_2OH$ | 274–276 | A | 67 | |
| 11 | $(CH_2)_4OH$ | 233–234 | B | 72 | $CH_2Cl_2$:hex |
| 12 | $CH_2CH(OCH_3)_2$ | 172–173 | B | 57 | |
| 13 | $(CH_2)_2CN$ | 268–270 | B | 43 | |
| 14 | $(CH_2)_3N(CH_3)_2$ | 169–171 | A | 27 | EA |
| 15 | $(CH_2)_2N(CH_2CH_3)_2$ | 212–216 (S) | B | 54 | |
| 16 | $(CH_2)_3N(CH_2CH_3)_2$ | 195–197 | B | 39 | |
| 17 | $(CH_2)_2NH(CH_2)_2OH$ | 158 (d)(S) | B | 34 | iPrOH |
| 18 | $(CH_2)_2$-1-pyrrolidinyl | 248–250 | B | 54 | |
| 19 | $(CH_2)_2$-1-piperidinyl | 234 (d)(S) | B | 49 | |
| 20 | $(CH_2)_2$-4-(morpholino) | 264–265 | B | 95 | Acetone |
| 21 | $(CH_2)_2$2-(1-$CH_3$)pyrrolidinyl | 203–205 | B | 33 | |
| 22 | $C_6H_5$ | 210 (d) | A | 31 | EtOH |
| 23 | 4-$CH_3OC_6H_4$ | 212–215 | A | 21 | EA |
| 24 | 4-$CH_3C_6H_4$ | 194–196 | A | 33 | |
| 25 | $C_6F_5$ | 198–214 | A | 49 | |
| 26 | 2-$CH_3OC_6H_4$ | 200 (d) | B | 70 | |
| 27 | 4-$HOC_6H_4$ | >300 | E | 71 | DMF |
| 28 | 1-naphthyl | 280–282 | B | 42 | |
| 29 | 2-pyridinyl | 259–261 | B | 63 | |
| 30 | 4-pyridinyl | 287–289 | B | 30 | Acetone |
| 31 | $CH_2C_6H_5$ | 243–245 | D | 47 | |
| 32 | $CH_2$-2-$CH_3OC_6H_4$ | 213–215 | B | 58 | $Et_2O$ |
| 33 | $CH_2$-2-$HOC_6H_4$ | 265–269 | E | 45 | |
| 34 | $CH_2$-4-$CH_3OC_6H_4$ | 196–198 | B | 70 | |
| 35 | $CH_2$-4-$HOC_6H_4$ | 302–303 | E | 56 | |
| 36 | $CH_2$-3,4,5-$(CH_3O)_3C_6H_2$ | 228–230 | B | 86 | |
| 37 | $(CH_2)_2C_6H_5$ | 221–223 | B | 72 | |
| 38 | $(CH_2)_2$-2-$CH_3OC_6H_4$ | 230–232 | B | 100 | |
| 39 | $(CH_2)_2$-2-$HOC_6H_4$ | >300 | E | 50 | |
| 40 | cyclohexyl | 259–261 | D | 52 | |
| 41 | cyclopentyl | 259–260 | B | 83 | |
| 42 | cycloheptyl | 248–250 | B | 47 | |
| 43 | $CH_2$-cyclohexyl | 190–193 | C | 31 | $Et_2O$ |
| 44 | 1,2,3,4-tetrahydro-2-naphthyl | 225–235 | B | 52 | Acetone |
| 45 | cis-2-$CH_3O$-cyclohexyl | 210–212 | B | 62 | |
| 46 | 4-tetrahydropyranyl | 282–284 | B | 86 | |
| 47 | 4-$CH_3$-cyclohexyl | 200–204 | B | 51 | |
| 48 | 4-$C_6H_5$-cyclohexyl | 152–207 | B | 44 | |
| 49 | 4-piperidinyl | 240 (d) | B | 80 | |
| 50 | 1-$CH_3$-4-piperidinyl | 218 (d) | B | 62 | |
| 51a | (cis)4-$(CH_3)_2$N-cyclohexyl* | 137–140 | B | 14 | |
| 51b | (trans)4-$(CH_3)_2$N-cyclohexyl* | 156–159 | B | 26 | |
| 52a | (cis)4-$CH_3CONH$-cyclohexyl* | 282 (d) | C | 5 | |
| 52b | (trans)4-$CH_3CONH$-cyclohexyl* | 245 (d) | C | 3 | |

*Isomers separated by chromatography

EXAMPLE 53

2-[5-Cyclopropyl-6,8-difluoro-2,5-dihydro-7-(2,6-dimethyl-4-pyridinyl)-3-oxo-3H-pyrazolo[4,3-c]quinolinyl]acetic acid. A mixture of example compound 9 (0.29 g, 0.00064 mol), acetic acid (3.2 mL), water (0.8 mL), and 12N HCl (0.8 mL) was heated at 100° C. for 3 h. After concentration, the residue was taken up in DMF, chilled, and filtered. The filtrate was concentrated and the resulting solid was slurried in THF. The solid was collected and washed with ether to give 0.21 g (73%) of a compound of formula I [$R_1=R_2=CH_3$, $R_3$=hydrogen, $R_4$=fluoro, $R_5=CH_2COOH$], mp 200° C.(d).

EXAMPLE 54

5-Cyclopropyl-6,8-difluoro-2,5-dihydro-2-[4-(dimethylamino)-butyl]-7-(2,6-dimethyl-4-pyridinyl)-3H-pyrazolo[4,3-c]quinolin-3-one. p-Toluenesulfonyl chloride (0.24 g, 1.25 mol) was added to a mixture of example compound 11 (Formula I $R_1=R_2=CH_3$, $R_3$=hydrogen, $R_4$=fluoro, $R_5=(CH_2)_4OH$) (0.42 g, 0.96 mmol) and 15 mL pyridine. The mixture was heated at 50° C. for 3 h and additional p-toluenesulfonyl chloride (0.050 g) was added followed by continued heating for another 1 h. The reaction mixture was poured into 1N HCl and was washed with ether. The aqueous portion was basified with 1N NaOH to pH 7.8 and was extracted with $CH_2Cl_2$. After drying ($Na_2SO_4$) the extracts were concentrated to give 0.26 g of crude rosylate which was dissolved in 15 mL ethanol saturated with dimethylamine. The resulting mixture was heated in a stainless steel pressure vessel at 110° C. for 2 hours. The reaction mixture was cooled and concentrated to give a crude product that was purified by silica gel chromatography to give 0.143 g (35%) of a compound of formula I [$R_1=R_2=CH_3$, $R_3$=hydrogen, $R_4$=fluoro. $R_5=(CH_2)_4N(CH_3)_2$], mp 173°–175° C.

EXAMPLE 55

2-[[2-(2,2-Bis(hydroxymethyl)ethylamino]ethyl]-5-cyclopropyl-6,8-difluoro-2,5-dihydro-7-(2,6-dimethyl-4-pyridinyl)-3H-pyrazolo[4,3-c ]quinolin-3-one. To a stirred suspension of example compound 10 (Formula I $R_1=R_2=CH_3$, $R_3$=hydrogen, $R_4$=fluoro, $R_5=(CH_2)_2OH$) (1.326 g, 3.23 mmol) in pyridine (7 mL) was added p-toluenesulfonyl chloride (0.74 g, 3.9 mmol). After warming on a steam bath at 60° C. for 75 min, the clear solution was evaporated on a rotary evaporator to leave a semi-crystalline solid (2.53 g) . To this crude tosylate was added diisopropylethylamine (10 mL and 2-amino-2-methyl-1,3-propanediol (11.4 g) . The mixture was stirred at reflux under $N_2$ for 15 min cooled. The upper mobile liquid layer was decanted and the remaining hard glassy material was taken up in warm water (75 mL). The solution was filtered, then extracted with $CH_2Cl_2$ (2×50 mL). The extracts were washed with water, dried ($MgSO_4$) and evaporated to afford a golden-yellow solid (0.544 g). Purification of the crude product was effected by silica gel chromatography to give a compound of formula I [$R_1=R_2=CH_3$, $R_3$=hydrogen, $R_4$=fluoro, $R_5=(CH_2)_2NHC(CH_2OH)_2CH_3$](0.106 g, 6.4%) as an amorphous solid.

EXAMPLE 56

2-(Cis-4-Aminocyclohexyl)-5-cyclopropyl-6,8-difluoro-2,5-dihydro-7-(2,6-dimethyl-4-pyridinyl)-3H-pyrazolo-[4,3-c]quinolin-3-one (56a) and 2-(trans-4-aminocyclohexyl)-5-cyclopropyl-6,8-difluoro-2,5 dihydro-7-(2,6-dimethyl-4-pyridinyl)-3H-pyrazolo[4,3-c]quinolin-3-one (56b). The unseparated isomers of example 52 (0.3 g, 0.59 mmol) and 2N HCl (27 mL) were heated at reflux for 14 h. The resulting solution was basified with $Na_2CO_3$ and extracted with $CH_2Cl_2$. The organic portion was dried ($Na_2CO_3$) and concentrated to give a crude product containing the isomeric amines. Purification of each isomer was done by silica gel chromatography to give 0.10 g (38%) of the cis isomer, a compound of formula I [$R_1=R_2=CH_3$, $R_3$=hydrogen, $R_4$=fluoro, $R_5$=(cis) 4-amino cyclohexyl], example 56a, mp 260°–260° C.; and 0.070 g (25%) of the trans isomer, example 56b, a compound of formula I [$R_1=R_2=CH_3$, $R_3$=hydrogen, $R_4$=fluoro, $R_5$=(trans) 4-amino cyclohexyl], mp 225°–228° C.

EXAMPLE 57

2-(cis-4-formamidocyclohexyl)-5-cyclopropyl-6,8-difluoro-2,5-dihydro-7-(2,6-dimethyl -4-pyridinyl)-3H-pyrazolo[4,3-c]quinolin-3-one A solution containing example compound 56a (0.144 g, 0.31 mmol) and N,N-dimethylformamide dimethyl acetal (10 mL) was heated at 50° C. for 13 h and concentrated. The crude product was purified using silica gel chromatography to give 0.124 g (77%) of a compound of formula I ($R_1=R_2=CH_3$, $R_3$=hydrogen, $R_4$=fluoro, $R_5$=(cis) 4-formamidocyclohexyl), mp 250° C. (decomposed).

EXAMPLE 58

2-(trans-4-formamidocyclohexyl)-5-cyclopropyl-6,8-difluoro-2,5-dihydro-7-(2,6-dimethyl-4-pyridinyl)-3H-pyrazolo[4,3-c]quinolin-3-one A solution containing example compound 56b (0.092 g, 0.00012 mol) and N,N-dimethylformamide dimethyl acetal (10 mL) was heated at 50° C. for 10 h and concentrated. The crude product was purified using silica gel chromatography to give 0.53 g (53%) of a compound of formula I [$R_1=R_2=CH_3$, $R_3$=hydrogen, $R_4$=fluoro, $R_5$=(trans) 4-formamido-cyclohexyl), mp 165°–167° C.

It is contemplated that the following intermediates of formula II, as described in U.S. Pat. No. 5,075,319, which is incorporated herein by reference, when esterified and thionylated as described in preparations 1 and 2 above, yield corresponding intermediates of formula IV;

1-cyclopropyl-6-fluoro-1,4-dihydro-7-(2,6-di(trifluoromethyl)-4-pyridinyl)-4-oxo-3-quinoline carboxylic acid, 1-cyclopropyl-6,8-difluoro-1,4-dihydro-7-(2-ethyl,6-hydroxymethyl)-4-pyridinyl) -4-oxo-3-quinoline carboxylic acid, 1-cyclopropyl-5,6, 8-trifluoro-1,4-dihydro-7-(2-methyl,6-methoxymethyl-4-pyridinyl) -4-oxo-3-quinolinone carboxylic acid, 1-cyclopropyl-6-fluoro-1,4-dihydro-7-(2-ethyl,6-chloromethyl) -4-pyridinyl)-4-oxo-3-quinoline carboxylic acid, and 1-cyclopropyl-6-fluoro-1,4-dihydro-7-(2-isopropyl,6-methylaminomethyl-4-pyridinyl) -4-oxo-3-quinoline carboxylic acid.

It is further contemplated that compounds of formula I are prepared from any of these intermediates by condensation with any of the example hydrazines, using methods A–D above.

BIOLOGICAL PROPERTIES

Topoisomerase II has been identified as the cellular target for a number of therapeutically important antineoplastic classes of drugs (Glisson and Ross, Pharmacol. Ther. 32, 89–106, 1987; Liu, Ann. Rev. Biochem. 58, 351–375, 1989). These chemically distinct agents include intercalating anthracyclines, aminoacridines, and ellipticines as well as the non-DNA intercalating epipodophyllotoxins. The intracellular effects of these agents (Zwelling et al., Biochem, 20, 6553–6563, 1981; Long et al,, Biochem. 23, 1183–1188, 1984; Rowe et al. Biochem. Pharmacol. 34, 2483–2487, 1985; Rowe et al., Cancer Res. 46, 2021–2026, 1986; Kerrigan et al., NCI Monographs 4:117–121, 1987; Covey et al., Cancer Res. 48, 860–865, 1988), in addition to their topoisomerase II reactivity in vitro (Nelson et al., Proc. Natl. Acazd, Sci. 81, 1361–1365, 1984; Tewey et al., J. Biol. Chem. 259, 9182–9187, 1984a; Tewey et al., Science 266, 466–468, 1984b; Ross et al., Cancer Res. 44, 5857–5860, 1984; Chen et al., J. Biol. Chem. 259, 13560–13566, 1984; Rowe et al., Cancer Res. 46, 2021–2026, 1986), implicate topoisomerase II inhibition as central to the cytotoxicity and antitumor activity of these antineoplastic agents. Additionally the mechanisms of resistance observed in several antineoplastic agent resistant cell lines appears to be a consequence of either an alteration in the topoisomerase enzyme molecule (Pommier et al., Cancer Res. 46, 3075–308a, 1986; Glisson et al., Cancer Res. 46, 1934–1938, 1986; Esty et al., Biochem. Biophys. Res. Commun. 144, 787–793, 1987; Danks et al., Biochem. 27, 8861–8869, 1988; Sinha et al., Cancer Res. 48, 5096–5100, 1988) or its level (Per et al., Mol. Pharmacol. 32, 17–25, 1987). This evidence has clearly established topoisomerase II inhibition as a means of deriving an antitumor effect.

The compounds of the present invention are inhibitors of mammalian topoisomerase II, thus indicating their use as cytotoxic and antineoplastic agents in the chemotherapy of cancer in mammals.

MAMMALIAN TOPOISOMERASE II INHIBITION ASSAY PROCEDURE

The inhibition of human topoisomerase II (hereafter topo II) was quantitated by a procedure adapted from that described by Trask et al., EMBO J., 3, 671–676 (1984). The assay quantitates the amount of topo II covalently attached to DNA at equilibrium during a topo II reaction. This assay determines the potential of a compound to stabilize this complex, which potential is closely related to the cytotoxicity of the compound.

Topo II was purified from late log phase suspension cultures of HeLa WIS by an adaptation of the method described by Per et al., Mol. Pharmacol., 32, 17–25 (1987).

Assays (in duplicate) were assembled at 4° C. Assay mix (25 µl) was distributed in Beckman (No. 265270) 1.5 mL microtiter tubes followed by the addition of 5 µl test compound to yield the final concentrations of assay components:
50 mM Tris-Cl pH 7.9
44 mM NaCl
10 mM $MgCl_2$
0.6 mM DTT
0.5 mM EDTA
30 µg/ml BSA
0.5 mM ATP
5.5% (w/v)glycerol
0.4 ng 3' end labeled ($^{32}$p) pBR322 DNA ($10^7$ DPM/µg)
10 units Topo II The assay mix including the test compound was incubated for 20 minutes at 37° C. The reaction was terminated at 37° C. by the addition of 3 µl 10% SDS followed by the addition of 266 µl 10 mM Tris-Cl pH 7.5, 20 µg/ml BSA, 20 µg/ml calf thymus DNA, 1% SDS.

A SDS/protein precipitate was formed by the addition of 28 µl 2.5M KCl followed by chilling on ice for a minimum of 10 minutes. The precipitate was collected and washed with a Brandell cell harvester on a GFB glass fiber filter membrane as follows. The contents of the assay tube were drawn up into the harvester. The tube was then rinsed 7× with 10 mM Tris-Cl pH 7.5, 1 mM EDTA and 100 mM KCl. The precipitate was washed with 1 L of a solution of 10 mM Tris-Cl pH 7.5, 1 mMEDTA, 100 mM KCl followed by 1 L of 95% ethyl alcohol and finally 0.5 L 70% of ethyl alcohol (per 48 samples in each case). After drying, CPM was determined by liquid scintillation counting with 5 ml Biofluor (NEN Research Products) or Readisafe (Beckman Instruments Inc.) cocktail.

Preparation of test compound—A stock solution (6 mg/ml) of test compound was prepared either in 0.1N sodium hydroxide or 0.2N hydrogen chloride. This solution then was diluted 1/5 into water and serially thereafter in either 0.02N sodium hydroxide or 0.04N hydrogen chloride, respectively. The stock solution and serial dilution of the test compound was stored at −20° C. prior to testing.

Screening of test compound—As an initial screen, the test compound was tested at a final concentration of 2, 20 and 200 µg/ml. The compound was then retested at a range of concentrations (usually 2–3×steps) bridging their approximate $EC_{50}$'s, as estimated by the prescreen.

Controls—A solvent control which indicates the base level of topo II-DNA complex formed in the absence of the test compound was included in each test. A control, in which topo II was omitted, was included for each test compound at the highest drug concentration tested.

Reference Agent—A dose response curve with mAMSA at 0.01, 0.08, 0.16, 0.32, 1.0 and 10 µg/ml was included in each test.

Data reduction—The $EC_{50}$ (effective concentration at which 50% of the maximal DNA-topo II complex is formed) of a test compound is defined to be the concentration with activity equal to the $EC_{50}$ of the reference agent, mAMSA. The maximal DNA-topo II complex formed is taken as that equal to that formed at the nearly saturating dose of mAMSA (10 µg/ml).

The results obtained for representative compounds of the invention in the human topoisomerase II assay procedure expressed as $EC_{50}$s (µM) are presented in Table II below.

MAMMALIAN CANCER CELL CYTOTOXICITY ASSAYS

In vitro cytotoxicity was assayed by determining cell survival following exposure of P388 murine leukemia cells to a range of test compound concentrations. Cytotoxicity was quantitated following either a one-hour exposure or continuous exposure of P388 cells to test compound.

Cytotoxicity following a one-hour exposure of cells to drug was assayed by quantitating clonogenic cell survival according to a published procedure [Freshney, R. L. (1987) Culture of Animal Cells. A Manual of Basic Technique. Wiley-Liss Inc., New York, NY, pp. 140–144]. Briefly, following drug exposure cells were plated in soft agar and incubated (37°, 5% $CO_2$) for 7–10 days during which time viable cells form visible colonies. Cytotoxicity following continuous exposure of cells to test compound was assayed by quantitating total P388 cells on a Coultier Counter following a 48-hour co-incubation of test compound with cells. P388 cells were maintained in log phase throughout the duration of cytotoxicity assays.

The percentage of cells surviving relative to an untreated control was graphed as a function of increasing drug concentration. The $IC_{50}$ is defined as that concentration of drug which reduced the population of viable cells to 50% that of an untreated control.

TABLE II

Topoisomerase Inhibition and In Vitro Cytotoxicity of Representative Examples of Compounds of Formula I

| Example | topo II inh.[a] $EC_{50}$ - µM | in vitro cytotoxicity[b] 1 hr exp. | cont. exp. |
| --- | --- | --- | --- |
| 1 | 2.6[c] | 0.26 | 0.04 |
| 2 | 6.8 | — | 1.4 |
| 3 | 5.0 | — | 0.53 |
| 4 | 2.9 | — | 1.5 |
| 5 | 1.2 | — | 0.15 |
| 6 | 11 | 7.9 | 3.6 |
| 7 | 5.9 | — | 0.51 |
| 8 | 6.9 | — | 3.5 |
| 9 | 6.1 | — | 0.15 |
| 10 | 6.4 | — | 1.4 |
| 11 | 4.2 | — | 0.88 |
| 12 | 23 | — | — |
| 13 | 6.7 | — | 1.4 |
| 14 | 1.7 | 0.16 | 0.38 |
| 15 | 93[c,d] | 0.45 | — |
| 16 | 6.0 | 0.49 | 1.2 |
| 17 | 3.3[c] | 1.3 | 1.2 |
| 18 | 650[c,d] | 0.3 | 0.035 |

TABLE II-continued

Topoisomerase Inhibition and In Vitro Cytotoxicity of Representative Examples of Compounds of Formula I

| Example | topo II inh.[a] EC$_{50}$ - μM | in vitro cytotoxicity[b] 1 hr exp. | cont. exp. |
|---|---|---|---|
| 19 | 210[c,d] | 0.44 | — |
| 20 | 48 | 2.8 | 0.41 |
| 21 | 3.5 | 0.33 | 0.16 |
| 22 | 2.7 | — | 0.84 |
| 23 | 6.8[c] | — | 5.2 |
| 24 | 8.9 | — | 4.9 |
| 25 | 3.4 | — | 2.2 |
| 26 | 5.0 | — | 0.34 |
| 27 | 4.9 | — | 2.6 |
| 28 | 2.9 | — | 0.32 |
| 29 | 2.8 | — | 0.74 |
| 30 | 8.0[c] | — | 1.2 |
| 31 | 3.7 | — | 0.14 |
| 32 | 5.1 | — | 1.2 |
| 33 | 3.8 | — | 1.4 |
| 34 | 3.2 | — | 0.44 |
| 35 | 1.5 | — | 0.25 |
| 36 | 6.4 | — | 1.2 |
| 37 | 5.0 | — | 2.2 |
| 38 | 11 | — | — |
| 39 | 9.6[c] | — | — |
| 40 | 0.90 | 0.68 | 0.19 |
| 41 | 4.0 | 1.1 | 0.38 |
| 42 | 2.9 | 4.2 | 1.5 |
| 43 | 8.2 | 6.7 | 4.9 |
| 44 | 3.7 | — | 1.5 |
| 45 | 6.3 | 0.57 | — |
| 46 | 1.7 | 0.29 | 0.25 |
| 47 | 3.1 | 1.4 | — |
| 48 | 4.5 | 8.4 | — |
| 49 | 5.6 | 2.3 | 2.5 |
| 50 | 3.2 | 0.094 | — |
| 51a | 1.7 | 0.067 | — |
| 51b | 4.4 | 0.26 | — |
| 52a | 7.4 | 1.3 | — |
| 52b | 9.8 | 1.2 | — |
| 53 | 10 | — | 18 |
| 54 | 15 | 0.40 | 0.50 |
| 55 | 11 | 11 | 25 |
| 56a | 0.5 | 0.44 | — |
| 56b | 4.2 | 1.5 | — |
| 57 | 0.80 | 5.1 | — |
| 58 | 1.5 | 9.1 | — |

[a]Effective concentration that achieves 50% of the maximal effect of m-AMSA vs topo II isolated from HeLa cells (see experimental section).
[b]Inhibitory concentration vs. P388 - IC50 - μM (see Biological Properties).
[c]Bell-shaped dose response curve was noted when determining IC$_{50}$.
[d]Extrapolated IC$_{50}$ value - 50% inhibition was not observed at the highest concentration of drug tested.

Representative examples of the compounds of formula I were also tested for antitumor activity in mice against several tumor systems, as described more fully below, and were found to possess antineoplastic activity as evidenced by their activity in reducing the size of and curing tumors, and increasing the survival time of the mice.

IN VIVO ANTITUMOR ASSAY PROCEDURE

Mice: Inbred: C3H/He and NCR-nu; and Hybrids: B6D2F1 (C57BL/6 females×DBA/2 males;' CD2F1 (Balb/c females×DBS/2 males) and B6C3fl (C57BL/6×C3H) were bred at Wayne State University from strains obtained from the Frederick Cancer Research Facility, Frederick, Maryland or purchased from commercial suppliers.

Tumors: Murine Tumor: P388 and an adriamycin-resistant (ADR) subline P388/ADR leukemia and the following transplantable solid tumors of mice were used for in vivo testing: B16 melanoma (B16), pancreatic ductal adenocarcinoma No. 03 (Panc 03), colon adenocarcinoma No. 38 (colo 38), lung carcinoma No. 12 (LC 12), mammary ductal adenocarcinoma No. 16/C (Mam16C) and an adriamycin-resistant subline Mam16-C/ADR. Human tumor: A single human tumor, mammary carcinoma MX-1 was used for in vivo testing. All tumors are in the Developmental Therapeutics Program frozen tumor respository, maintained by the Biological Testing Branch, Frederick Maryland. Each has a detailed description, code identification number, and list of references at the National Tumor Repository. Murine tumors were maintained in the mouse strain of origin and were transplanted in the appropriate F1 hydrid (or the strain of origin) for therapy trials. Human mammary carcinoma MX-1 (MX1) was maintained as a subcutaneous implant in either athymic Swiss (Cr: NIH(S)-nu) or athymic random bred (NCR-nu) mice and transplanted in NCR-nu for therapy trials.

Chemotherapy: For pancreatic ductal adenocarcinoma No. 3, colon adenocarcinoma No. 38 (colo 38), lung carcinoma No. 12 LC 12) and both adriamycin-sensitive (RP) and-resistant (ADR) mammary ductal adenocarcinoma No. 16 (Mam16) tumors, bilateral tumor implants were used to help ensure a more uniform tumor burden per mouse (thus reducing the requirement for greater numbers of mice per group). The animals necessary to begin an experiment were pooled, implanted bilaterally s.c. on day zero with 30–60 mg tumor fragments using a 12-gauge trocar, and again pooled before randomization to the various treatment and control groups. Chemotherapy was started within three days after tumor implantation while the number of cells per mouse was relatively small ($1 \times 10^7 - 1 \times 10^8$ cells).

For P388 and P388/ADR leukemia studies the tumor cells were implanted either interperitoneally (IP) or intravenously (IV) on day zero and treatment was started on day one. For B16 melanoma (B16) studies, the tumor cells were implanted IP on day zero and treatment was started on day one. Titered controls were also included to facilitate the calculation of tumor cell kill. For mammary carcinoma MX-1 studies, tumors were implanted with 1) subcutaneously (sc) (14-mg fragment of sc donor tumor) in the axillary region or 2) under the subrenal capsule (SRC) (10×10×10 ocular micrometer unit fragment of sc donor tumor). Treatment started on the day after subrenal capsule tumor implant or when the subcutaneous tumor implant had reached 100–700 mg.

END POINTS FOR ASSESSING ANTITUMOR ACTIVITY

Quantitative end points used to assess antitumor activity included % Increased Life Span (% ILS), Tumor Cell Kill (Log$_{10}$ kill), and Tumor Growth Inhibition (T/C). Long Term Survivors (45 or 60 day) were excluded from calculations of %ILS and Tumor Cell Kill. Endpoints were calculated as follows:

% ILS $$\% ILS = \frac{D_t - D_c}{D_c} (100)$$

where $D_t$ is the median day of death for treated and $D_c$ is the median day of death for control groups. A % ILS $\geq 20$ or $\geq 25$ for P388 and B16 intraperitoneal models, respectively, is indicative of a significant degree of antitumor activity. A % ILS $\geq 75$ or $\geq 50$ for P388 and B16 intraperitoneal models, , respectively, is indicative of a high degree of antitumor activity and is the level used by National Cancer Institute to justify further development if other requirements are met (termed DN-2 level activity). Minimum quantitative activity limits for additional P388 models (e.g. P388/ADR and P388, IV) have not been defined. However, the activity limits specified for the intraperitoneal models may be applied as in the majority of instances the intraperitoneal models are found to be signficantly less challenging.

TUMOR CELL KILL

The $\log_{10}$ cell kill was calculated from the following formula:

$$\text{Log}_{10} \text{ kill (total)} = \frac{T-C}{(3.32)(Td)}$$

where $T-C$ is the tumor difference in the median day of death between the treated (T) and the control (C) groups and Td is the tumor doubling time (in days), the latter estimated from the best fit straight line from a log-linear growth plot of the control-group tumors in exponential growth. The conversion of the $T-C$ values to $\log_{10}$ cell kill is possible because the Td for tumors regrowing post-treatment approximated the Td values of the tumors in untreated control mice.

T/C VALUE

Tumors were measured with a caliper once or twice weekly (as needed) until either tumors exceeded 1600 mg or cure was assured. Tumor weights were estimated from two-dimensional measurements: Tumor Weight $(mg) = (a \times b^2) / 2$, where a and b are the tumor length and width (ram) respectively. Measurements were carried out simultaneously in both treatment and control groups. When the control group tumors reached approximately 750–1500 mg in size (median of group), the median tumor weight of each group was determined (including zeros). The T/C value in percent is an indication of antitumor effectiveness. The % T/C was calculated from the following formula for solid murine tumor models:

$$\% \ T/C = \frac{T}{C} \times 100$$

where T and C are median tumor weights of the treatment and control groups, respectively. A T/C equal to or less than 42% is considered significant antitumor activity. A T/C value <10% is indicative of a high degree of antitumor activity and is the level used by National Cancer Institute to justify further development if other requirements are met (termed DN-2 level activity). By convention the T/C value for the mammary carcinoma MX-1 models is calculated by the parameter of change in tumor weight . The % T/C was calculated from the following formula for MX-1 models $$\% \ T/C = \frac{\Delta T}{C} \times 100 \ (\text{if } \Delta T \text{ is positive})$$

$$\% \ T/C = \frac{\Delta T}{T(\text{initial})} \times 100 \ (\text{if } \Delta T \text{ is negative})$$

where $\Delta T$ and $\Delta C$ are the change in mean tumor weight of the test and control groups, respectively, and T (initial) is the initial mean tumor weight of the test group. An initial % T/C $\leq 20$ is considered necessary to demonstrate moderate activity. A reproducible % T/C $\leq 10$ is considered significant activity.

ACTIVITY

In vivo trials of representative examples of the compounds of formula I are summarized in Table III.

TABLE III

In vivo Properties of Representative Examples of Compounds of Formula I

| Example | Exp | Model | Drug Route | Schedule | MTD Mg/Kg | T/C % | ILS % | Log Kill |
|---|---|---|---|---|---|---|---|---|
| 1 | SD-17 | B16(ip) | ip | qd 1,5,9 | 78 | | 85 | 1.9 |
| | 1038 | Colo38(sc) | iv, sc | iv; qd 3–16 | 58 | 0 | | 1.2 |
| | 1038 | Colo38(sc) | iv | qd 3,7,11 | 78 | 14 | | 0.60 |
| | 1161 | LC12(sc) | iv | qd 3,5 | 35[1] | 25 | | 0.76 |
| | 924 | Mam16C/RP (sc) | iv | bid 1–5 | 20 | 13 | | 1.2 |
| | 1120A | Mam16C/ADR | iv | qd 1,3,5 | 58[2] | 26 | | 0.50 |
| | 1132 | Mam16C(sc) | iv | qd 1–4 | 43 | 7 | | 1.3 |
| | 1142A | Mam16C(sc) | iv | qd 1,3,5 | 43 | 18 | | 1.9 |
| | SD-9 | MXI(sc) | ip | qd 1,5,9 | 78 | 37 | | |
| | SD-18 | MXI(src) | ip | qd 1,5,9 | 52 | 6 | | |
| | 1073B | P388/ADR(iv) | iv | qd 1–5 | 48 | | 14.3 | 0.93 |
| | 1149B | P388/ADR(iv) | iv | qd 1–3 | 52 | | 27 | 1.3 |
| | 1155A | P388(iv) | iv | qd 1–3 | 37 | | 82 | 5.4 |
| | SD-7 | P388(ip) | iv | qd 1,5,9 | 117 | | 170 | 12 |
| | SD-7 | P388(ip) | ip | qd 1,5,9 | 78 | | 155 | 11 |
| | 895A | Panc03(sc) | iv | qd 3 | 35 | 32 | | 0.66 |
| | 910 | Panc03(sc) | iv | qd 3–9 | 45 | 45 | | |
| | 1005A | Panc03(sc) | iv | qd 3,4 | 52 | 66 | | |
| | 1146 | Panc03(sc) | iv | qd 3,6,9 | 34 | 8 | | 0.66 |
| 6 | 783 | Panc03(sc) | sc | qd 16–18 qd 3–13 | 2500[1] | >100 | | |
| 14 | SD-17 | B16(ip) | ip | qd 1,5,9 | 28 | | 58[3] | 1.3 |
| | 905 | Colo38(sc) | iv | qd 3,12–14 | 133 | 38 | | 0.54 |
| | 924 | Mam16C/RP | iv | bid 1–8 | 101 | 8 | | 1.5 |
| | SD-9 | MXI(sc) | ip | qd 1,5,9 | 42 | 53 | | |
| | SD-7 | P388(ip) | iv | qd 1,5,9 | 64 | | 70 | 5.0 |
| | SD-7 | P388(ip) | ip | qd 1,5,9 | 42 | | 85 | 6.1 |
| | 910 | Panc03(sc) | iv | bid 3–13 | 107 | 16 | | |
| | 895A | Panc03(sc) | iv | qd 3–5 | 64 | 35 | | 0.60 |
| 17 | SD-17 | B16(ip) | ip | qd 1,5,9 | 180 | | 61 | 1.4 |
| | SD-9 | MXI(sc) | ip | qd 1,5,9 | 270 | 67 | | |
| | SD-7 | P388(ip) | iv | qd 1,5,9 | 120 | | 5 | 0.35 |

TABLE III-continued

In vivo Properties of Representative Examples of Compounds of Formula I

| Example | Exp | Model | Drug Route | Schedule | MTD Mg/Kg | T/C % | ILS % | Log Kill |
|---|---|---|---|---|---|---|---|---|
| | SD-7 | P388(ip) | ip | qd 1,5,9 | 180 | | 50 | 3.5 |
| | 988 | Panc03(sc) | iv,sc | iv; qd 3,9–11 bid 4–5,12–15 sc; bid 16,18 qd 17,19 | 1410 | 42 | | |
| 21 | 1097 | Panc03(sc) | iv | qd 3–4 | 80 | 35 | | |
| 22 | 861 | Panc03(sc) | sc | qd 3–7 | 635 | >100 | | |
| 23 | 887B | panc03(sc) | sc | qd3–8 | 1150 | 18 | | |
| | 953 | Panc03(sc) | iv | (3-hr continuous infusion) | 140 | 18 | | |
| 50 | 1086 | Panc03(sc) | iv | qd 3–14 | 128 | 24 | | |
| 51a | SD-17 | B16(ip) | ip | qd 1,5,9 | 15[1] | | 29[2,3] | 0.67 |
| | 1036 | Colo38(sc) | iv | qd 3–4 bid 5,6,12–17 | 63 | 39 | | |
| | SD-18 | MXI(src) | ip | qd 1,5,9 | 23[1] | 5 | | |
| | SD-15 | P388(ip) | iv | qd 1,5,9 | 39.9 | | 70 | 5.1 |
| | SD-16 | P388(ip) | ip | qd 1,5,9 | 9.9 | | 65 | 4.7 |
| | 1005A | Panc03(sc) | iv | qd 3–4,8–12 | 63 | 5 | | |
| 51b | SD-17 | B16(ip) | ip | qd 1,5,9 | 99[1] | | 47[2,3] | 1.0 |
| | 1036 | Colo38(sc) | iv | qd 3–4,15,17 bid 5-7 | 220[1] | 13[1] | | |
| | SD-18 | MXI(src) | ip | qd 1,5,9 | 99 | 2 | | |
| | SD-16 | P388(ip) | iv | qd 1,5,9 | 120 | | 85 | 6.2 |
| | SD-16 | P388(ip) | ip | qd 1,5,9 | 66 | | 85 | 6.2 |
| | 1005A | Panc03(sc) | iv,sc | iv; qd 3–4, 8–14 sc; bid 15, | 390[1] | 2 | | |
| 56a | 1163 | Colo38(sc) | iv,sc | iv; qd 3–9 sc; qd 11–19 | 137 | 40 | | |
| | 1086 | Panc03(sc) | iv | qd 3–4, 8–14 | 110 | 21 | | |
| 56b | 1086 | Panc03(sc) | iv,sc | iv; qd 3–6 bid 7–12 sc; qd 15 bid 13–14 | 550 | 42 | | |

[1]MTD not achieved-maximum dose tested.
[2]2 lower doses equally active to modestly more active.
[3]1/6 tumor free long term survivor.

In practicing the method of the invention, the therapeutic dose of the compound of formula I to be administered to the mammal afflicted with malignant cells is that amount which is effective to inhibit mammalian topoisomerase II and thereby to inhibit the growth of, kill or induce the regression of the malignant cells, or to prolong the life of the mammal.

The specific amount of formula I constituting a therapeutically effective dose and the length of treatment required will vary since it is dependent on a number of factors such as, for example, the size, age, condition and species of the mammal to be treated, the degree of involvement of the malignancy, the specific compound to be administered and its bioavailability, the dose regimen and the mode of administration. The specific amount to be employed for a particular afflicted mammal is readily determinable by the skilled artisan using conventional techniques.

In practicing the invention, the compounds can be administered to the mammal orally or parenterally.

The compounds can be prepared for use by incorporating them in conventional, pharmaceutically acceptable diluents, carriers or excipients. For parenteral administration (intravenous, intraperitoneal, subcutaneous or intramuscular), the compounds are dissolved or suspended in an aqueous or nonaqueous vehicle. For oral administration, the compounds are formulated in dosage unit form as tablets or capsules. Exemplary diluents, carriers or excipients include lactose, dextrose, sucrose, sorbitol, mannitol, starches, gum acacia, calcium phosphate, mineral oil, cocoa butter, alginates, tragacanth, gelatin, methyl cellulose, methyl- and propyl hydroxybenzoates, talc, magnesium stearate and the like.

I claim:

1. A compound of formula

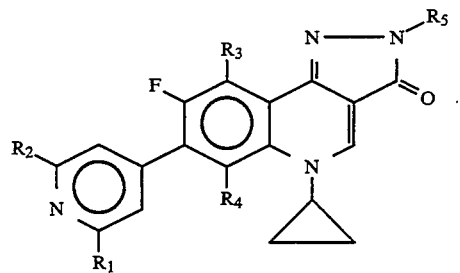

wherein
$R_1$ is hydrogen, lower-alkyl, or trifluoromethyl;
$R_2$ is lower-alkyl, trifluoromethyl or $CH_2Y$ where Y is hydroxy, chloro, lower-alkylamino or diloweralkylamino
$R_3$ and $R_4$ are each independently hydrogen or fluoro;
$R_5$ is hydrogen, lower-alkyl or
  (a) phenyl, 2-pyridyl, 4-pyridyl, 1-naphthyl or such groups substituted with one to about three, the same or different, lower-alkyl, fluoro, hydroxy, or lower-alkoxy;
  (b) $C_4$ to $C_7$ cycloalkyl or $C_4$ to $C_7$ cycloalkyl substituted with amino, lower-alkylamino, diloweralkylamino, formamido, acetamido, lower-alkyl, hydroxy, lower-alkoxy, trifluoromethyl, carboxy, lower-alkoxycarbonyl or halo, or $C_4$ to $C_7$ cycloalkyl having a phenyl ring fused thereto, forming a $C_8$ to $C_{11}$ bicyclic radical wherein 1 ring is aromatic and the other saturated;

(c) A saturated carbon containing heterocyclic 5- or 6-membered ring containing oxygen and/or nitrogen or such ring substituted with lower-alkyl where if both nitrogen and oxygen are present they are non-adjacent; or (d) $(CH_2)_n$-Z wherein n is an integer from one to four and Z is amino, dilower-alkylamino, bis(hydroxylower-alkyl) lower-alkylamino, hydroxy, trifluoromethyl, carboxy, lower-alkoxycarbonyl, lower-alkoxy, formyl or acetal thereof, or a substituent selected from (a), (b) or (c); or a pharmaceutically acceptable acid addition salt thereof.

2. A compound according to claim 1 wherein $R_1$ and $R_2$ are methyl, $R_3$ is hydrogen, and $R_4$ is fluoro.

3. A compound according to claim 2 wherein $R_5$ is hydrogen, 2-pyridyl, 4-pyridyl, phenyl, 1-naphthyl or phenyl substituted with one or more of fluoro, methyl, methoxy or hydroxy.

4. A compound according to claim 2 wherein $R_5$ is a cyclopentyl, cyclohexyl, cycloheptyl, or 1,2,3,4-tetrahydro-2-naphthyl, or cyclohexyl substituted with dimethylamino, amino, acetamido or formamido.

5. A compound according to claim 2 wherein $R_5$ is piperidinyl, tetrahydropyranyl, pyrrolidinyl or piperidinyl substituted with methyl.

6. A compound according to claim 2 wherein $R_5$ is $(CH_2)_nZ$, n is 1-3 and Z is phenyl, phenyl substituted in the 2 or 4 position with methoxy or hydroxy, 3,4,5$(CH_3O)_3$ phenyl, ethoxy carbonyl, bis (hydroxymethyl) ethylamino, hydroxy, diethylamino, dimethylamino, 2-hydroxyethylamino, cyano, cyclohexyl, acetamido, tetrahydropyranyl, 1-pyrrolidinyl, 1-piperidinyl, 4-morpholino or 2-(1-$CH_3$)-pyrrolidinyl.

7. A compound according to claim 2 wherein $R_5$ is hydrogen, phenyl, cyclohexyl, 2(N,N-dimethylamino)ethyl, 3(N,N-dimethylamino)propyl, 2-(N-hydroxyethylamino)ethyl, 2-(1-methyl-2-pyrrolidinyl)ethyl, 4(N,N-dimethylamino)-cyclohexyl, 4-aminocyclohexyl, 4-(N-methylamino)cyclohexyl.

8. A compound according to claim 6 having the formula

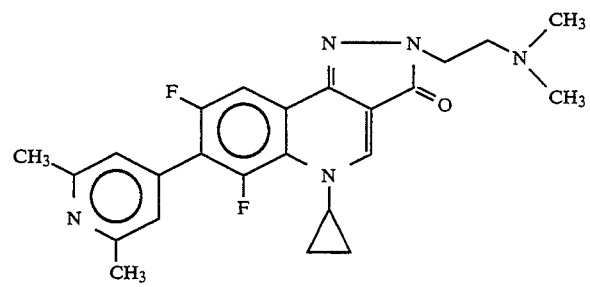

9. A pharmaceutical composition comprising a carrier and as an active ingredient a compound according to claim 1 in a sufficient amount to inhibit the growth of malignant cells susceptable to the action of such compound.

10. A pharmaceutical composition comprising a carrier and as an active ingredient a compound according to claim 2 in a sufficient amount to inhibit the growth of malignant cells susceptable to the action of such compound.

11. A pharmaceutical composition comprising a carrier and as an active ingredient a compound according to claim 3 in a sufficient amount to inhibit the growth of malignant cells susceptable to the action of such compound.

12. A pharmaceutical composition comprising a carrier and as an active ingredient a compound according to claim 4 in a sufficient amount to inhibit the growth of malignant cells susceptable to the action of such compound.

13. A pharmaceutical composition comprising a carrier and as an active ingredient a compound according to claim 5 in a sufficient amount to inhibit the growth of malignant cells susceptable to the action of such compound.

14. A pharmaceutical composition comprising a carrier and as an active ingredient a compound according to claim 6 in a sufficient amount to inhibit the growth of malignant cells susceptable to the action of such compound.

15. A pharmaceutical composition comprising a carrier and as an active ingredient a compound according to claim 7 in a sufficient amount to inhibit the growth of malignant cells susceptable to the action of such compound.

16. A pharmaceutical composition comprising a carrier and as an active ingredient a compound according to claim 8 in a sufficient amount to inhibit the growth of malignant cells susceptable to the action of such compound.

* * * * *

UNITED STATES PATENT AND TRADEMARK OFFICE
CERTIFICATE OF CORRECTION

PATENT NO. : 5,334,595
DATED : August 2, 1994
INVENTOR(S) : Mark P. Wentland

It is certified that error appears in the above-indentified patent and that said Letters Patent is hereby corrected as shown below:

Column 17, line 33, "and width (ram) respectively." should read
--and width (mm) respectively--.

Signed and Sealed this

Eighteenth Day of October, 1994

Attest:

BRUCE LEHMAN

*Attesting Officer*  *Commissioner of Patents and Trademarks*